(12) United States Patent
Helton et al.

(10) Patent No.: US 7,795,266 B2
(45) Date of Patent: Sep. 14, 2010

(54) TETRAHYDROINDOLONE DERIVATIVES FOR TREAMENT OF NEUROLOGICAL CONDITIONS

(76) Inventors: David R. Helton, 19 Avignon Ave., Foothill Ranch, CA (US) 92610; David B. Fick, 6 Mojo Ct., Newport Beach, CA (US) 92663; Jason P. Sharp, 2903 Bonanza, San Clemente, CA (US) 92673; Ernest H. Pfadenhauer, 2821 Portola Dr., Costa Mesa, CA (US) 92626

( * ) Notice: Subject to any disclaimer, the term of this patent is extended or adjusted under 35 U.S.C. 154(b) by 742 days.

(21) Appl. No.: 10/595,219

(22) PCT Filed: Sep. 27, 2004

(86) PCT No.: PCT/US2004/031743

§ 371 (c)(1), (2), (4) Date: Nov. 16, 2006

(87) PCT Pub. No.: WO2005/030148

PCT Pub. Date: Apr. 7, 2005

(65) Prior Publication Data

US 2007/0208030 A1     Sep. 6, 2007

Related U.S. Application Data

(60) Provisional application No. 60/505,692, filed on Sep. 25, 2003.

(51) Int. Cl.
| | |
|---|---|
| A61K 31/497 | (2006.01) |
| A61K 31/519 | (2006.01) |
| A61K 31/33 | (2006.01) |
| A01N 43/90 | (2006.01) |
| A01N 43/00 | (2006.01) |
| C07D 403/00 | (2006.01) |
| C07D 241/04 | (2006.01) |
| C07D 295/00 | (2006.01) |
| C07D 231/56 | (2006.01) |
| C07D 487/00 | (2006.01) |
| C07D 209/04 | (2006.01) |
| C07D 209/52 | (2006.01) |
| C09B 5/00 | (2006.01) |

(52) U.S. Cl. .................. 514/254.09; 514/265.1; 514/183; 544/373; 544/402; 548/360.1; 548/516; 548/416; 548/469

(58) Field of Classification Search ............ 514/254.09, 514/265.1, 183; 544/373, 402; 548/360.1, 548/516, 416, 469
See application file for complete search history.

(56) References Cited

U.S. PATENT DOCUMENTS

| | | | |
|---|---|---|---|
| 3,621,027 A | 11/1971 | Schoen et al. | |
| 4,260,762 A | 4/1981 | Berger et al. | |
| 4,349,678 A | 9/1982 | Berger et al. | |
| 4,442,291 A | 4/1984 | Berger et al. | |
| 5,585,378 A | 12/1996 | Boar et al. | |
| 5,661,184 A | 8/1997 | Helton et al. | |
| 5,717,109 A | 2/1998 | Arnold et al. | |
| 5,916,920 A | 6/1999 | Fernandez et al. | |
| 5,925,630 A | 7/1999 | Upasani et al. | |
| 5,925,680 A | 7/1999 | Helton et al. | |
| 6,242,462 B1 | 6/2001 | Bleakman et al. | |
| 6,258,807 B1 | 7/2001 | Helton et al. | |
| 6,395,766 B1 | 5/2002 | Broughton et al. | |
| 6,444,665 B1 | 9/2002 | Helton et al. | |
| 6,465,472 B1 | 10/2002 | Upasani et al. | |
| 6,630,478 B2 | 10/2003 | Diamond et al. | |
| 6,630,490 B2 | 10/2003 | Diamond et al. | |
| 6,680,332 B1 | 1/2004 | Konkoy et al. | |
| 6,759,427 B2 | 7/2004 | Fick et al. | |
| 6,770,638 B2 | 8/2004 | Fick et al. | |
| 6,780,853 B1 | 8/2004 | Upasani et al. | |
| 6,790,848 B2 | 9/2004 | Briggs et al. | |
| 6,800,657 B2 | 10/2004 | Konkoy et al. | |
| 6,982,269 B2 | 1/2006 | Glasky et al. | |
| 7,247,633 B2 | 7/2007 | Nilsson | |
| 7,309,703 B2 | 12/2007 | Beavers et al. | |
| 2002/0040031 A1 | 4/2002 | Glasky et al. | |
| 2002/0040032 A1 | 4/2002 | Glasky et al. | |
| 2002/0055506 A1 | 5/2002 | Diamond et al. | |
| 2002/0061899 A1 | 5/2002 | Diamond et al. | |
| 2002/0091133 A1 | 7/2002 | Taylor | |
| 2002/0128264 A1 | 9/2002 | Taylor | |

(Continued)

FOREIGN PATENT DOCUMENTS

AU    716665 B2    7/1997

(Continued)

OTHER PUBLICATIONS

Declaration of David Helton Under 37 C.F.R. Section 1.132, 8 pages.

(Continued)

Primary Examiner—Sreeni Padmanabhan
Assistant Examiner—Samira Jean-Louis
(74) Attorney, Agent, or Firm—Michael Fedrick; Loza & Loza, LLP

(57) ABSTRACT

Compositions comprising tetrahydroindolone derivatives in which the tetrahydroindolone moiety is covalently linked to a substituted arylpiperazine moiety and methods for treating neurological and psychiatric conditions using such compositions are disclosed.

6 Claims, No Drawings

U.S. PATENT DOCUMENTS

| | | |
|---|---|---|
| 2002/0198218 A1 | 12/2002 | Fick et al. |
| 2003/0022892 A1 | 1/2003 | Glasky et al. |
| 2003/0045527 A1 | 3/2003 | Briggs et al. |
| 2003/0114463 A1 | 6/2003 | Fick et al. |
| 2005/0096317 A1 | 5/2005 | Glasky et al. |
| 2005/0107439 A1 | 5/2005 | Helton et al. |
| 2005/0159790 A1 | 7/2005 | Shalev |
| 2006/0020299 A1 | 1/2006 | Shalev |
| 2006/0025420 A1 | 2/2006 | Brauns et al. |
| 2006/0079520 A1 | 4/2006 | Singh et al. |

FOREIGN PATENT DOCUMENTS

| | | | |
|---|---|---|---|
| GB | 2352632 A | | 7/2001 |
| WO | WO9962899 A1 | | 12/1999 |
| WO | WO01/16103 A1 | | 3/2001 |
| WO | WO02/04450 A2 | | 1/2002 |
| WO | WO03011396 A1 | | 2/2003 |
| WO | WO03035072 A1 | | 5/2003 |

OTHER PUBLICATIONS

International Preliminary Report on Patentability, Form PCT/IPEA/409, PCT/US04/31743, International Filing Date Sep. 27, 2004, Priority Date, Sep. 25, 2003, 3 pages.

Response to Written Opinion Under Article 34, 8 pages.

European Search Report dated Jun. 15, 2009, EP04785168.8-2112/1715921 PCT/US2004031743.

Ramesh Narayanan, et al. "Selective androgen receptor modulators in preclinical and clinical development", Nuclear Receptor Signaling, The Open Access Journal of the Nuclear Receptor Signaling Atlas, 2008, vol. 6, 26 pgs.

BP Nutley, et al. Preclinical pharmacokinetics and metabolism of a novel prototype DNA-PK inhibtor NU7026, British Jouranl of Cancer (2005) 93, pp. 1011-1018.

H. Tecle, et al. "CI-1017, a functionally M1-selective muscarinic agonist: design, synthesis, and preclinical pharmacology", Pharmaceutica Acta Helvetiae 74 (2000) pp. 141-148.

TETRAHYDROINDOLONE DERIVATIVES FOR TREAMENT OF NEUROLOGICAL CONDITIONS

This application claims priority from PCT International Patent Application No. PCT/US2004/031743, filed on Sep. 27, 2004, entitled "TETRAHYDROINDOLONE DERIVATIVES FOR TREATMENT OF NEUROLOGICAL CONDITIONS," which claims priority from U.S. Provisional Patent Application No. 60/505,692, filed on Sep. 25, 2003, entitled "Composition and method for treating pain and pain-induced psychiatric disorders."

BACKGROUND

Psychiatric and neurological conditions can be extremely difficult to treat effectively because of the multiplicity of symptoms and etiologies associated with such conditions. Current drug therapies have focused on either high selectivity for one pharmacological effect or broad non-selectivity to attempt to provide multiple symptom relief. Therapies that have focused on high pharmacological selectivity have been shown to provide limited benefits for disorders with multiple causes, but can in some cases worsen some symptoms. For example, selective antagonism of dopaminergic receptors for schizophrenia results in a worsening of some negative symptoms as well as in tardive dyskinesia.

Drug therapies having broad non-selectivity, on the other hand, can provide relief for more symptoms but often have more side effects. For instance, current antipyschotic drugs have adrenergic, cholinergic, and histaminergic receptor antagonist activities that are associated with deterioration of cognitive function and other side-effects, such as orthostatic hypotension, dry mouth, blurred vision, constipation, and motor impairment. Regardless of drug therapy selectivity, there remain symptoms, such as cognitive decline, that are not adequately treated by current pharmaceutical compounds used in treating psychiatric and neurological conditions. A need therefore remains for improved pharmaceutical compounds for use in treating such conditions.

SUMMARY

We have discovered that the combination tetrahydroindolone arylpiperazine compounds described herein can be useful for treating many different psychiatric and neurological conditions, including but not limited to pain, emesis, neurodegeneration including neuropathies, and psychiatric disorders, as described below.

DETAILED DESCRIPTION

Definitions

As used herein, the following terms have the following meanings, unless explicitly stated otherwise.

The term "alkyl" refers to saturated aliphatic groups including straight-chain, branched-chain, and cyclic groups, all of which can be optionally substituted. Preferred alkyl groups contain 1 to 10 carbon atoms. Suitable alkyl groups include methyl, ethyl, and the like, and can be optionally substituted. The term "heteroalkyl" refers to carbon-containing straight-chained, branch-chained and cyclic groups, all of which can be optionally substituted, containing at least one O, N or S heteroatoms. The term "alkoxy" refers to the ether —O-alkyl, where alkyl is defined as above.

The term "alkenyl" refers to unsaturated groups which contain at least one carbon-carbon double bond and includes straight-chain, branched-chain, and cyclic groups, all of which can be optionally substituted. Preferable alkenyl groups have 2 to 10 carbon atoms. The term "heteroalkenyl" refers to unsaturated groups which contain at least one carbon-carbon double bond and includes straight-chained, branch-chained and cyclic groups, all of which can be optionally substituted, containing at least one O, N or S heteroatoms.

The term "aryl" refers to aromatic groups that have at least one ring having a conjugated, pi-electron system and includes carbocyclic aryl and biaryl, both of which can be optionally substituted. Preferred aryl groups have 6 to 10 carbon atoms. The term "aralkyl" refers to an alkyl group substituted with an aryl group. Suitable aralkyl groups include benzyl and the like; these groups can be optionally substituted. The term "aralkenyl" refers to an alkenyl group substituted with an aryl group. The term "heteroaryl" refers to carbon-containing 5-14 membered cyclic unsaturated radicals containing one, two, three, or four O, N, or S heteroatoms and having 6, 10, or 14-electrons delocalized in one or more rings, e.g., pyridine, oxazole, indole, thiazole, isoxazole, pyrazole, pyrrole, each of which can be optionally substituted as discussed above.

The term "sulfonyl" refers to the group —S(O$_2$)—. The term "halo" refers to fluoro-, chloro-, bromo-, or iodo-substitutions. The term "alkanoyl" refers to the group —C(O)Rg, where Rg is alkyl. The term "aroyl" refers to the group —C(O)Rg, where Rg is aryl. Similar compound radicals involving a carbonyl group and other groups are defined by analogy. The term "aminocarbonyl" refers to the group —NHC(O)—. The term "oxycarbonyl" refers to the group —OC(O)—. The term "heteroaralkyl" refers to an alkyl group substituted with a heteroaryl group. Similarly, the term "heteroaralkenyl" refers to an alkenyl group substituted with a heteroaryl group.

The term "optionally substituted" refers to one or more substituents which can be, without limitation, alkyl, aryl, amino, hydroxy, alkoxy, aryloxy, alkylamino, arylamino, alkylthio, arylthio, or oxo, cyano, acetoxy, or halo moieties.

As used herein, the term "derivative" refers to a compound that is modified or partially substituted with another component. Additionally, the term "derivative" encompasses compounds that can be structurally similar but can have similar or different functions. The term "pharmacophore" refers to a structural component of a molecule that causes a pharmacological response. The terms "patient," "subject" and the like with reference to individuals that can be treated with the present compounds and/or pharmaceutical compositions refer to humans and other mammals.

The terms "a," "an," and "the" and similar referents used in the context of describing the present invention are to be construed to cover both the singular and the plural, unless otherwise indicated herein or clearly contradicted by context. Recitation of value ranges herein is merely intended to serve as a shorthand method for referring individually to each separate value falling within the range. Unless otherwise indicated herein, each individual value is incorporated into the specification as if it were individually recited herein.

Compounds

The compounds of the present invention have the general schematic structure {A}-L-{B}, where A is a tetrahydroindolone derivative, L is a hydrocarbyl chain, and B is an arylpiperazine derivative, as described below.

Tetrahydroindolone Derivatives

In the compounds of the present invention, the tetrahydroindolone derivatives ("THI") have the structure of formula (I) below:

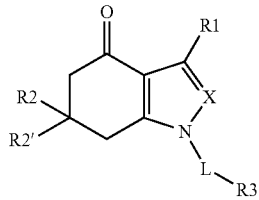

where:
(a) X is CH or N;
(b) $R_1$ is hydrogen, alkyl, aralky, heteroaralkyl, alkenyl, aralkenyl, heteroaralkenyl, aryl, or heteroaryl;
(c) $R_2$ is hydrogen, alkyl, aralky, aryl, or heteroaryl;
(d) $R_{2'}$ is hydrogen unless $R_2$ is methyl, in which case $R_{2'}$ is also methyl; and
(e) L and $R_3$ are as described below.

As shown in Formula (I), the THI moiety has a six-membered saturated ring fused to a five-membered aromatic ring. The five-membered aromatic ring can have one or two nitrogen atoms as indicated, but the five-membered aromatic ring always has a nitrogen atom at the 1-position. Typically, the five-membered aromatic ring has one nitrogen atom as in tetrahydroindolone. This nitrogen atom at the 1-position is covalently bonded to the linker L.

Typically, X is carbon in the tetrahydroindolone moiety. The THI moiety can be variously substituted, as described above. One example of such a tetrahydroindolone moiety is a tetrahydroindolone moiety of formula (D) below:

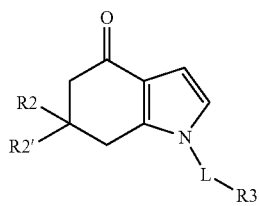

where:
(1) $R_2$ is hydrogen, alkyl, aralkyl, heteroaralkyl, aryl or heteroaryl;
(2) $R_{2'}$ is hydrogen unless $R_2$ is methyl, in which case $R_{2'}$ is also methyl; and
(3) L and $R_3$ are as described below.

In one particularly preferred embodiment, $R_2$ and $R_{2'}$ are both hydrogen. In this embodiment, the THI moiety is an unsubstituted tetrahydroindolone moiety.

Arylpiperazine Moiety

The R3 group referred to above is an arylpiperazine moiety, which in the compounds of the present invention has the structure of formula (III) below:

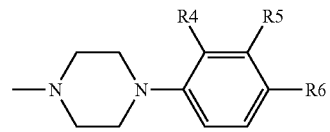

where:
(i) $R_4$ is hydrogen, alkyl, halo, hydroxy, alkoxy, cyano, nitro, perfluoroalkyl, perfluoroalkoxy, or hydroxymethyl;
(ii) $R_5$ is hydrogen, alkyl, halo, alkoxy, cyano, nitro, perfluoroalkyl, perfluoroalkoxy, amino, aminocarbonyl, aminosulfonyl, or hydroxymethyl;
(iii) $R_6$ is alkyl, halo, alkoxy, perfluoroalkyl, perfluoroalkoxy, or nitro;
(iv) $R_4$ and $R_5$ when taken together can form a 5 or 6 membered ring and can contain one or more heteroatoms; and
(v) $R_5$ and $R_6$ when taken together can form a 5 or 6 membered ring and can contain one or more heteroatoms.

Preferably, the aryl piperazine moiety comprises one or more of the following substitutions:
(i) $R_4$ is hydrogen, halo, or alkoxy;
(ii) $R_5$ is hydrogen, alkyl, halo, alkoxy, or perfluoroalkyl;
(iii) $R_6$ is alkyl, halo, alkoxy, or perfluoroalkyl;
(iv) $R_4$ and $R_5$ when taken together form a naphthalene ring; and
(v) $R_5$ and $R_6$ when taken together can be either a methylenedioxy or ethylenedioxy group.

Linker Moiety

The linker moiety (L) used in the compounds of the present invention can be a straight chain alkyl group of the formula $-(CH_2)_m-$, where m is an integer from 1 to 6 and more preferably either 3, 4, or 5. Alternatively, the linker can be an alkyl substituted hydrocarbyl moiety of the following formula (IV):

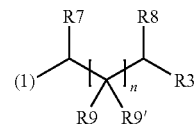

where:
(i) n is 0, 1 or 2;
(ii) R7 and R8 are hydrogen, methyl or ethyl;
(iii) R9 and R9' are both hydrogen, methyl or ethyl;
(iv) if n is 1 and R7 or R8 is methyl or ethyl, then R9 and R9' are hydrogen;
(v) if n is 1 and R7 and R8 are hydrogen, then R9 and R9' are methyl or ethyl; and
(vi) if n is 2, then R9 and R9' are hydrogen and one or both of R7 and R8 are methyl or ethyl.

The linker moiety can modulate properties of the present compounds. For example, a straight chain alkyl linker comprising two carbon atoms would provide a more rigid linkage than a longer alkyl linker. Such rigidity can produce greater specificity in target binding, while a less rigid linker moiety can produce greater potency. The solubility characteristics of the present compounds can also be affected by the nature of the linker moiety.

The use of a linker according to formula (IV) above is believed to provide a more rigid linkage compared to a straight chain linker moiety with the same number of carbon atoms in the chain. This allows for further control over the properties of the present compounds.

Moreover, a linker according to formula (IV) can be used with compounds other than those described herein which comprise a THI moiety (which can be variously substituted) joined to an arylpiperazine moiety (which also can be variously substituted) via such a linker. Such THI moieties and other compounds are described, for example, in U.S. Pat. No. 6,770,638 (the contents of which are hereby incorporated by reference).

Preferred Compounds

Table 1 below lists particularly preferred embodiments of the present compounds.

TABLE 1

1  1-{2-[4-(4-Fluorophenyl)piperazin-1-yl]ethyl}-1,5,6,7-tetrahydroindol-4-one
2  1-{3-[4-(4-Fluorophenyl)piperazin-1-yl]propyl}-1,5,6,7-tetrahydroindol-4-one
3  1-{4-[4-(4-Fluorophenyl)piperazin-1-yl]butyl}-1,5,6,7-tetrahydroindol-4-one
4  1-{2-[4-(4-Chlorophenyl)piperazin-1-yl]ethyl}-1,5,6,7-tetrahydroindol-4-one
5  1-{3-[4-(4-Chlorophenyl)piperazin-1-yl]propyl}-1,5,6,7-tetrahydroindol-4-one
6  1-{4-[4-(4-Chlorophenyl)piperazin-1-yl]butyl}-1,5,6,7-tetrahydroindol-4-one
7  1-{2-[4-(4-Methoxyphenyl)piperazin-1-yl]ethyl}-1,5,6,7-tetrahydroindol-4-one
8  1-{3-[4-(4-Methoxyphenyl)piperazin-1-yl]propyl}-1,5,6,7-tetrahydroindol-4-one
9  1-{4-[4-(4-Methoxyphenyl)piperazin-1-yl]butyl}-1,5,6,7-tetrahydroindol-4-one
10 1-{2-[4-(4-Ethoxyphenyl)piperazin-1-yl]ethyl}-1,5,6,7-tetrahydroindol-4-one
11 1-{3-[4-(4-Ethoxyphenyl)piperazin-1-yl]propyl}-1,5,6,7-tetrahydroindol-4-one
12 1-{4-[4-(4-Ethoxyphenyl)piperazin-1-yl]butyl}-1,5,6,7-tetrahydroindol-4-one
13 1-{2-[4-(4-Trifluoromethylphenyl)piperazin-1-yl]ethyl}-1,5,6,7-tetrahydroindol-4-one
14 1-{3-[4-(4-Trifluoromethylphenyl)piperazin-1-yl]propyl}-1,5,6,7-tetrahydroindol-4-one
15 1-{4-[4-(4-Trifluoromethylphenyl)piperazin-1-yl]butyl}-1,5,6,7-tetrahydroindol-4-one
16 1-{2-[4-(4-Nitrophenyl)piperazin-1-yl]ethyl}-1,5,6,7-tetrahydroindol-4-one
17 1-{3-[4-(4-Nitrophenyl)piperazin-1-yl]propyl}-1,5,6,7-tetrahydroindol-4-one
18 1-{4-[4-(4-Nitrophenyl)piperazin-1-yl]butyl}-1,5,6,7-tetrahydroindol-4-one
19 1-{2-[4-p-Tolylpiperazin-1-yl]ethyl}-1,5,6,7-tetrahydroindol-4-one
20 1-{3-[4-p-Tolylpiperazin-1-yl]propyl}-1,5,6,7-tetrahydroindol-4-one
21 1-{4-[4-p-Tolylpiperazin-1-yl]butyl}-1,5,6,7-tetrahydroindol-4-one
22 1-{2-[4-(4-Trifluoromethoxyphenyl)piperazin-1-yl]ethyl}-1,5,6,7-tetrahydroindol-4-one
23 1-{3-[4-(4-Trifluoromethoxyphenyl)piperazin-1-yl]propyl}-1,5,6,7-tetrahydroindol-4-one
24 1-{4-[4-(4-Trifluoromethoxyphenyl)piperazin-1-yl]butyl}-1,5,6,7-tetrahydroindol-4-one
25 1-{2-[4-(3,4-Dichlorophenyl)piperazin-1-yl]ethyl}-1,5,6,7-tetrahydroindol-4-one
26 1-{3-[4-(3,4-Dichlorophenyl)piperazin-1-yl]propyl}-1,5,6,7-tetrahydroindol-4-one
27 1-{4-[4-(3,4-Dichlorophenyl)piperazin-1-yl]butyl}-1,5,6,7-tetrahydroindol-4-one
28 1-{2-[4-(3,4-Difluorophenyl)piperazin-1-yl]ethyl}-1,5,6,7-tetrahydroindol-4-one
29 1-{3-[4-(3,4-Difluorophenyl)piperazin-1-yl]propyl}-1,5,6,7-tetrahydroindol-4-one
30 1-{4-[4-(3,4-Difluorophenyl)piperazin-1-yl]butyl}-1,5,6,7-tetrahydroindol-4-one
31 1-{2-[4-(3,4-Dimethylphenyl)piperazin-1-yl]ethyl}-1,5,6,7-tetrahydroindol-4-one
32 1-{3-[4-(3,4-Dimethylphenyl)piperazin-1-yl]propyl}-1,5,6,7-tetrahydroindol-4-one
33 1-{4-[4-(3,4-Dimethylphenyl)piperazin-1-yl]butyl}-1,5,6,7-tetrahydroindol-4-one
34 1-{2-[4-(3,4-Dimethoxyphenyl)piperazin-1-yl]ethyl}-1,5,6,7-tetrahydroindol-4-one
35 1-{3-[4-(3,4-Dimethoxyphenyl)piperazin-1-yl]propyl}-1,5,6,7-tetrahydroindol-4-one
36 1-{4-[4-(3,4-Dimethoxyphenyl)piperazin-1-yl]butyl}-1,5,6,7-tetrahydroindol-4-one
37 1-[2-(4-Benzo[1,3]dioxol-5-ylpiperazin-1-yl)ethyl]-1,5,6,7-tetrahydroindol-4-one
38 1-[3-(4-Benzo[1,3]dioxol-5-ylpiperazin-1-yl)propyl]-1,5,6,7-tetrahydroindol-4-one
39 1-[4-(4-Benzo[1,3]dioxol-5-ylpiperazin-1-yl)butyl]-1,5,6,7-tetrahydroindol-4-one
40 1-{2-[4-(2,3-Dihydrobenzo[1,4]dioxin-6-yl)piperazin-1-yl]ethyl}-1,5,6,7-tetrahydroindol-4-one
41 1-{3-[4-(2,3-Dihydrobenzo[1,4]dioxin-6-yl)piperazin-1-yl]propyl}-1,5,6,7-tetrahydroindol-4-one
42 1-{4-[4-(2,3-Dihydrobenzo[1,4]dioxin-6-yl)piperazin-1-yl]butyl}-1,5,6,7-tetrahydroindol-4-one
43 1-{2-[4-(2,4-Dichlorophenyl)piperazin-1-yl]ethyl}-1,5,6,7-tetrahydroindol-4-one
44 1-{3-[4-(2,4-Dichlorophenyl)piperazin-1-yl]propyl}-1,5,6,7-tetrahydroindol-4-one
45 1-{4-[4-(2,4-Dichlorophenyl)piperazin-1-yl]butyl}-1,5,6,7-tetrahydroindol-4-one
46 1-{2-[4-(2,4-Difluorophenyl)piperazin-1-yl]ethyl}-1,5,6,7-tetrahydroindol-4-one
47 1-{3-[4-(2,4-Difluorophenyl)piperazin-1-yl]propyl}-1,5,6,7-tetrahydroindol-4-one
48 1-{4-[4-(2,4-Difluorophenyl)piperazin-1-yl]butyl}-1,5,6,7-tetrahydroindol-4-one
49 1-{2-[4-(2,4-Dimethylphenyl)piperazin-1-yl]ethyl}-1,5,6,7-tetrahydroindol-4-one
50 1-{3-[4-(2,4-Dimethylphenyl)piperazin-1-yl]propyl}-1,5,6,7-tetrahydroindol-4-one
51 1-{4-[4-(2,4-Dimethylphenyl)piperazin-1-yl]butyl}-1,5,6,7-tetrahydroindol-4-one
52 1-{2-[4-(2,4-Dimethoxyphenyl)piperazin-1-yl]ethyl}-1,5,6,7-tetrahydroindol-4-one
53 1-{3-[4-(2,4-Dimethoxyphenyl)piperazin-1-yl]propyl}-1,5,6,7-tetrahydroindol-4-one
54 1-{4-[4-(2,4-Dimethoxyphenyl)piperazin-1-yl]butyl}-1,5,6,7-tetrahydroindol-4-one
55 1-{2-[4-(2,3,4-Trichlorophenyl)piperazin-1-yl]ethyl}-1,5,6,7-tetrahydroindol-4-one
56 1-{3-[4-(2,3,4-Trichlorophenyl)piperazin-1-yl]propyl}-1,5,6,7-tetrahydroindol-4-one
57 1-{4-[4-(2,3,4-Trichlorophenyl)piperazin-1-yl]butyl}-1,5,6,7-tetrahydroindol-4-one
58 1-{2-[4-(2,3,4-Trifluorophenyl)piperazin-1-yl]ethyl}-1,5,6,7-tetrahydroindol-4-one
59 1-{3-[4-(2,3,4-Trifluorophenyl)piperazin-1-yl]propyl}-1,5,6,7-tetrahydroindol-4-one
60 1-{4-[4-(2,3,4-Trifluorophenyl)piperazin-1-yl]butyl}-1,5,6,7-tetrahydroindol-4-one
61 1-{2-[4-(3-Chloro-4-fluorophenyl)piperazin-1-yl]ethyl}-1,5,6,7-tetrahydroindol-4-one
62 1-{3-[4-(3-Chloro-4-fluorophenyl)piperazin-1-yl]propyl}-1,5,6,7-tetrahydroindol-4-one
63 1-{4-[4-(3-Chloro-4-fluorophenyl)piperazin-1-yl]butyl}-1,5,6,7-tetrahydroindol-4-one
64 1-{2-[4-(4-Fluoro-3-trifluoromethylphenyl)piperazin-1-yl]ethyl}-1,5,6,7-tetrahydroindol-4-one
65 1-{3-[4-(4-Fluoro-3-trifluoromethylphenyl)piperazin-1-yl]propyl}-1,5,6,7-tetrahydroindol-4-one
66 1-{4-[4-(4-Fluoro-3-trifluoromethylphenyl)piperazin-1-yl]butyl}-1,5,6,7-tetrahydroindol-4-one
67 1-{2-[4-(4-Chloro-2-methoxyphenyl)piperazin-1-yl]ethyl}-1,5,6,7-tetrahydroindol-4-one

TABLE 1-continued 68  1-{3-[4-(4-Chloro-2-methoxyphenyl)piperazin-1-yl]propyl}-1,5,6,7-tetrahydroindol-4-one
69  1-{4-[4-(4-Chloro-2-methoxyphenyl)piperazin-1-yl]butyl}-1,5,6,7-tetrahydroindol-4-one
70  1-{2-[4-(4-Chloro-3-trifluoromethylphenyl)piperazin-1-yl]ethyl}-1,5,6,7-tetrahydroindol-4-one
71  1-{3-[4-(4-Chloro-3-trifluoromethylphenyl)piperazin-1-yl]propyl}-1,5,6,7-tetrahydroindol-4-one
72  1-{4-[4-(4-Chloro-3-trifluoromethylphenyl)piperazin-1-yl]butyl}-1,5,6,7-tetrahydroindol-4-one
73  1-{2-[4-(3-Chloro-4-methoxyphenyl)piperazin-1-yl]ethyl}-1,5,6,7-tetrahydroindol-4-one
74  1-{3-[4-(3-Chloro-4-methoxyphenyl)piperazin-1-yl]propyl}-1,5,6,7-tetrahydroindol-4-one
75  1-{4-[4-(3-Chloro-4-methoxyphenyl)piperazin-1-yl]butyl}-1,5,6,7-tetrahydroindol-4-one
76  1-{2-[4-(4-Methoxy-3-trifluoromethylphenyl)piperazin-1-yl]ethyl}-1,5,6,7-tetrahydroindol-4-one
77  1-{3-[4-(4-Methoxy-3-trifluoromethylphenyl)piperazin-1-yl]propyl}-1,5,6,7-tetrahydroindol-4-one
78  1-{4-[4-(4-Methoxy-3-trifluoromethylphenyl)piperazin-1-yl]butyl}-1,5,6,7-tetrahydroindol-4-one
79  1-{2-[4-(4-Chloronaphthalen-1-yl)piperazin-1-yl]ethyl}-1,5,6,7-tetrahydroindol-4-one
80  1-{3-[4-(4-Chloronaphthalen-1-yl)piperazin-1-yl]propyl}-1,5,6,7-tetrahydroindol-4-one
81  1-{4-[4-(4-Chloronaphthalen-1-yl)piperazin-1-yl]butyl}-1,5,6,7-tetrahydroindol-4-one
82  1-{2-[4-(4-Trifluoromethylnaphthalen-1-yl)piperazin-1-yl]ethyl}-1,5,6,7-tetrahydroindol-4-one
83  1-{3-[4-(4-Trifluoromethylnaphthalen-1-yl)piperazin-1-yl]propyl}-1,5,6,7-tetrahydroindol-4-one
84  1-{4-[4-(4-Trifluoromethylnaphthalen-1-yl)piperazin-1-yl]butyl}-1,5,6,7-tetrahydroindol-4-one
85  1-{2-[4-(4-Chloro-2-fluorophenyl)piperazin-1-yl]ethyl}-1,5,6,7-tetrahydroindol-4-one
86  1-{3-[4-(4-Chloro-2-fluorophenyl)piperazin-1-yl]propyl}-1,5,6,7-tetrahydroindol-4-one
87  1-{4-[4-(4-Chloro-2-fluorophenyl)piperazin-1-yl]butyl}-1,5,6,7-tetrahydroindol-4-one
88  1-{2-[4-(4-Methoxy-2,3-dimethylphenyl)piperazin-1-yl]ethyl}-1,5,6,7-tetrahydroindol-4-one
89  1-{3-[4-(4-Methoxy-2,3-dimethylphenyl)piperazin-1-yl]propyl}-1,5,6,7-tetrahydroindol-4-one
90  1-{4-[4-(4-Methoxy-2,3-dimethylphenyl)piperazin-1-yl]butyl}-1,5,6,7-tetrahydroindol-4-one Properties Preferred compounds of the present invention have a logP of from about 1 to about 4 to enhance bioavailability and, when desired, central nervous system (CNS) penetration. Using this guideline, one of ordinary skill in the art can choose the appropriate arylpiperazine moieties for a particular THI moiety in order to ensure the bioavailability and CNS penetration of a compound of the present invention. For example, if a highly hydrophobic THI moiety is chosen, with particularly hydrophobic substituents, then a more hydrophilic arylpiperazine moiety can be used.

A number of compounds according to the present invention are optically active, owing to the presence of chiral carbons or other centers of asymmetry. In cases where compounds of the present invention are optically active, all of the possible enantiomers or diastereoisomers are included unless otherwise indicated despite possible differences in activity.

In general, the present compounds also include salts and prodrug esters of the compounds described herein. It is well known that organic compounds, including substituted tetrahydroindolones, arylpiperazines and other components of the present compounds, have multiple groups that can accept or donate protons, depending upon the pH of the solution in which they are present. These groups include carboxyl groups, hydroxyl groups, amino groups, sulfonic acid groups, and other groups known to be involved in acid-base reactions. The recitation of a compound in the present application includes such salt forms as occur at physiological pH or at the pH of a pharmaceutical composition unless specifically excluded.

Similarly, prodrug esters can be formed by reaction of either a carboxyl or a hydroxyl group on the compound with either an acid or an alcohol to form an ester. Typically, the acid or alcohol includes an alkyl group such as methyl, ethyl, propyl, isopropyl, butyl, isobutyl, and tertiary butyl. These groups can be substituted with substituents such as hydroxy, halo, or other substituents. Such prodrugs are well known in the art. The prodrug is converted into the active compound by hydrolysis of the ester linkage, typically by intracellular enzymes. Other suitable groups that can be used to form prodrug esters are well known in the art.

Synthesis Methods

In order to synthesize the tetrahydroindolone derivatives described herein, the tetrahydroindolone moiety is generally substituted with a linker which in turn is linked to the arylpiperazine moiety that completes the molecule. This route comprises either the steps of: (1) synthesizing an appropriately substituted tetrahydroindolone moiety linked to an aliphatic linker in which the linker is terminated with a halogen, and then reacting the halogen intermediate with the arylpiperazine to produce the final product; or (2) synthesizing an appropriately substituted arylpiperazine moiety linked to an aliphatic linker in which the linker is terminated with a halogen, and then reacting the halogen intermediate with the tetrahydroindolone to produce the final product.

Representative tetrahydroindazolone derivatives, as in formula (I) when X is N, can be made from appropriately substituted cyclohexanediones containing R2 and R2' substitutions via a two step procedure consisting of acylation with an acid chloride containing the R1 group in the presence of an amine base, followed by cyclization with an appropriately substituted arylpiperazine linked to a hydrazine moiety, usually heated under reflux in an aprotic solvent.

Another reaction that can be used to functionalize tetrahydroindolones is the Mitsunobu reaction. The Mitsunobu reaction is a highly versatile method for the introduction of widely varying functional groups on the tetrahydroindolone moiety, because of the wide assortment of primary and secondary alcohols that are commercially available for use in this reaction.

The length of the aliphatic linker covalently bound to the tetrahydroindolone moiety can be varied to change the distance between the tetrahydroindolone moiety and the arylpiperazine moiety in the compounds of the present invention.

The arylpiperazinyl moiety of the present compounds can be synthesized by a dihalide substitution reaction. Suitable substitution reactions are described, e.g., in M. B. Smith & J. March, "March's Advanced Organic Chemistry: Reactions, Mechanisms, and Structure" ($5^{th}$ ed., Wiley-Interscience, New York, 2001).

Representative arylpiperazines can be made by those skilled in the art from appropriately substituted anilines via a substitution/cyclization reaction with bis(2-chloroethyl)

amine. The compounds are generally mixed in the presence of a base (acid scavenger) in a protic solvent (such as alcohol) and heated.

SYNTHESIS EXAMPLES

The following representative methods for synthesizing exemplary embodiments of the present invention are merely intended as examples. Persons having ordinary skill in the art of medicinal and/or organic chemistry will understand that other starting materials, intermediates, and reaction conditions are possible. Furthermore, it is understood that various salts and esters of these compounds are also easily made and that these salts and esters can have biological activity similar or equivalent to the parent compound. Generally, such salts have halides or organic acids as anion counterions. However, other anions can be used and are considered within the scope of the present invention.

Example 1

Synthesis of 1-{2-[4-(3,4-Dichlorophenyl)piperazin-1-yl]ethyl}-1,5,6,7-tetrahydroindol-4-one Step 1: Preparation of 1-(2-Chloroethyl)-4-(3,4-dichlorophenyl)piperazine A mixture of (3,4-dichlorophenyl)piperazine (500 mg) and powdered sodium hydroxide (87 mg) in DMSO (5 mL) was treated with 2-bromo-1-chloroethane (387 mg) and stirred at ambient temperature for 16 hours. The reaction was poured into ice cold water (15 mL) and stirred for 0.5 hours. A solid mass formed and was separated by decanting the water. The aqueous layer was extracted with dichloromethane (5 mL). The solid mass was dissolved with dichloromethane (5 mL) and the combined organics were dried with sodium sulfate, filtered and the solvent removed under vacuum. Flash chromatography (dichloromethane:methanol 1:0 to 10:1) yielded an oil (230 mg) as the titled compound.

Step 2: 1-{2-[4-(3,4-Dichlorophenyl)piperazin-1-yl]ethyl}-1,5,6,7-tetrahydroindol-4-one To a solution of 1,5,6,7-tetrahyroindol-4-one (107 mg) in DMSO (2 mL) was added powdered sodium hydroxide (33 mg) and the mixture was stirred at ambient temperature for 0.5 hours. 1-(2-Chloroethyl)-4-(3,4-dichlorophenyl)piperazine (220 mg) from step 1 was then added as a solution in DMSO (2 mL) and the resulting mixture stirred at ambient temperature for 24 hours then heated to approximately 60° C. for 2 hours, after which time thin layer chromatography (TLC) (ethyl acetate:dichloromethane 1:1) showed complete reaction. The reaction was poured into ice cold water (15 mL) and stirred for 0.5 hours. A solid mass formed and was separated by decanting the water. The aqueous layer was extracted with dichloromethane (10 mL). The solid mass was dissolved with dichloromethane (5 mL) and the combined organics were dried with sodium sulfate and the solvent removed under vacuum to obtain an oil (250 mg) as the titled compound.

Step 3: Preparation of Oxalate salt of 1-{2-[4-(3,4-Dichlorophenyl)piperazin-1-yl]ethyl}-1,5,6,7-tetrahydroindol 4-one The compound from step 2 (250 mg) was dissolved in ethyl acetate (5 mL) using heat if required, and a solution of oxalic acid (57 mg) in acetone (0.5 mL) was added with stirring. A precipitate formed immediately and the mixture was stirred for 0.5 hours at room temperature. Vacuum filtration and washing with ethyl acetate afforded an off-white powder upon drying (220 mg).

The same 3-step procedure is used for all ethyl and propyl linkers.

Example 2

Synthesis of 1-{4-[4-(3,4-Dichlorophenyl)piperazin-1-yl]butyl}-1,5,6,7-tetrahydroindol-4-one Step 1: Synthesis of 1-(4-Chlorobutyl)-1,5,6,7-tetrahydroindol-4-one To a solution of 1,5,6,7-tetrahydroindol-4-one (10.0 g) in DMSO (100 mL) was added powdered sodium hydroxide (3.26 g) and the mixture was stirred at ambient temperature for 0.25 hours. 1-Bromo-4-chlorobutane (9.38 mL) was then added and the resulting mixture stirred at ambient temperature for 7 hours after which time TLC (ethyl acetate:dichloromethane 1:1) showed complete reaction. The reaction was poured into ice cold water (250 mL) and stirred for 0.5 hours. An oil separated and was isolated with a separatory funnel. The aqueous layer was extracted with dichloromethane (50 mL). The oil was dissolved with dichloromethane (25 mL) and the combined organics were dried with sodium sulfate, filtered and the solvent removed under vacuum. Flash chromatography (ethyl acetate:hexane, 1:1 to 2:1) yielded an oil (6.0 g) as the titled compound.

Step 2: Synthesis of 1-{4-[4-(3,4-Dichlorophenyl)piperazin-1-yl]butyl}-1,5,6,7-tetrahydroindol-4-one A mixture of 1-(4-Chlorobutyl)-1,5,6,7-tetrahydroindol-4-one (600 mg) from step 1 and sodium iodide (438 mg) in acetonitrile (10 mL) was heated at reflux for 6 hours. (3,4-Dichlorophenyl)piperazine (581 mg) and potassium carbonate (367 mg) was then added and reflux continued for 16 h. TLC (ethyl acetate:dichloromethane 1:1) showed complete reaction. The reaction was poured into ice cold water (50 mL) and stirred for 0.5 hours. An oil separated out and was isolated from the mixture. The oil was dissolved with dichloromethane (15 mL), washed with water and brine, then dried with sodium sulfate, filtered and the solvent removed under vacuum to yield the title compound as an oil (970 mg).

Step 3: Oxalate Salt Formation

Oxalate salt formation is done in the same manner as previously described.

The same 3-step procedure is used for all butyl linkers.

Treatments

Psychiatric Conditions

Psychiatric and neurological conditions can be treated by administering therapeutically effective amounts of the present compounds and/or pharmaceutical compositions. These compounds can be used as anti-psychotic compounds and administered to treat psychiatric disorders such as depression, anxiety including post traumatic stress syndrome, schizophrenia, schizoaffective disorders, bipolar disorders, sexual dysfunction, mood swings, sleep disorders, anorexia, bulimia, manic depression, obsessive compulsive disorders, delusional post-partum, depression, postpartum psychosis, pre-menstrual syndrome, drug abuse associated psychoses and combinations thereof. The present compounds can also be used to enhance cognitive function and to treat neuroregenerative disorders with cognitive deterioration such as Parkinson's disease, Huntington's disease, Alzheimer's disease, dementia associated with aging, and exposure to toxic chemical agents such as soman and saran.

The therapeutic effect of the compounds of the present invention is believed to be achieved by the ability of such compounds to affect multiple neuroreceptors. These compounds are thus believed to comprise multiple pharmacophores having different receptor activities. For example, the arylpiperazine moiety of the compounds is believed to affect dopamine and serotonin (5-HT) receptors. In particular, the arylpiperazine derivatives contained in the compound are believed to have dopamine D4 receptor antagonist activity and to have activity at other receptors including, but not limited to, dopamine D1, D2, and D3, as well as at serotonin receptors including but not limited to 5-HT1 (A-F), 5-HT2 (A-C), 5-HT3 (1-7), 5-HT4 C, 5-HT5 (A-B), 5-HT6, and 5-HT7.

Additionally, the tetrahydroindolone derivative moiety of the present compounds is believed to be a pharmacophore with GABA activity. As those skilled in the art will appreciate, GABA receptors are highly localized in the hippocampal region of the brain which is associated with memory. Generally recognized GABA receptors include, but are not limited to GABA A alpha (1-6), GABA A beta (1-3), GABA A gamma (1-3), GABA A delta, GABA A pi, GABA A theta, GABA A rho (1-3), GABA B1 (a-c), GABA B2, and GABA C. Pharmacophores having GABA activity are believed to enhance cognitive function.

In another embodiment of the present invention, pharmaceutical compounds disclosed herein can selectively modulate dopamine, GABA and/or serotonin receptors, in particular D4 receptors. A compound that "selectively modulates" refers to one that interacts preferentially with a receptor causing increases or decreases in related neurological functions compared with its interaction with other receptors.

Emotional, mood swings and cognitive disorders related to psychiatric disturbances that are expressed as sleep disorders, anorexia, bulimia, postpartum depression, post-partum psychosis, pre-menstrual syndrome, manic depression, obsessive compulsive disorders, and delusional disorders can also be treated using the present compounds and pharmaceutical compositions. Other emotional disturbances that can be effectively treated include those related to substance abuse. For example, the present pharmaceutical compositions can be used to prevent drug dependence or tolerance including that produced by nicotine, opioids such as morphine, cocaine and barbiturates such as diaxepam. Furthermore, the pharmaceutical compositions of the present invention can be useful in preventing or treating emotional and cognitive disturbances or psychoses associated with drug withdrawal or cessation tolerance including that produced by nicotine, opioids such as morphine, cocaine and barbiturates such as diaxepam.

Cognitive and other neurological disorders that can be effectively treated using the present compounds and pharmaceutical compositions include conditions such as, but not limited to, neurosensory diseases and injury, Parkinson's disease and other movement disorders such as dystonia, Wilson's disease, inherited ataxias, Tourette syndrome cerebral palsy, encephalopathies. Other cognitive conditions that can be treated include cognitive and attention deficit disorders associated with acquired immunodeficiency syndrome (AIDS), dementia, ischemic stroke, chemical exposure, and cardiac bypass associated cognitive defects.

The present invention thus includes the use of the present compounds in a pharmaceutical composition to treat psychiatric and neurological conditions as described above. In addition, the invention includes the use of these compounds for the manufacture of a medicament for the treatment of such psychiatric and neurological conditions.

Pain

Pain can be effectively treated with the compounds and pharmaceutical compositions of the present invention by administering an effective amount of these compounds and/or compositions to a patient in need thereof, in particular by administering an analgesic dosage of these compositions. Among the different types of pain that can be treated with the present compounds are acute pain, chronic pain, nociceptive pain (i.e., pain associated with pain transmission through intact nerve endings), and neuropathic pain (caused by nervous system dysfunction and characterized by burning, shooting, and tingling pain, associated with allodynia, hyperpathia, paresthesias and dysesthesias). Conditions which can involve acute pain include headache, arthritis, simple muscle strain, and dysmenorrhea. Nociceptive pain can include, e.g., post-operative pain, cluster headaches, dental pain, surgical pain, pain resulting from burns, post partum pain, angina pain, genitourinary tract related pain, cystitis, pain associated with arthritis, AIDS, chronic back pain, visceral organ pain, gastroesophageal reflux, peptic ulcers, infectious gastritis, inflammatory bowel disorders, misname headaches, tension headaches, fibromyalgia, nerve root compression such as sciatica, trigeminal neuralgia, central pain, bone injury pain, pain during labor and delivery, muscle strain, alcoholism, herpetic neuralgia, phantom limb paw and dysmenorrheal pain. Conditions involving neuropathic pain include chronic lower back pain, pain associated with arthritis, cancer-associated pain, herpes neuralgia, phantom limb pain, central pain, opioid resistant neuropathic pain, bone injury pain, and pain during labor and delivery. Relief from pain-induced psychiatric disorders such as anxiety, depression and/or severe mood changes as well as emetic responses related to pain and its treatment can also be provided with the present compounds and compositions.

In one embodiment, the compounds of the present application can be combined with other analgesics to form a pharmaceutical composition, in order to lower the dose of the present compounds required to relieve pain and/or to achieve a synergistic reduction in pain experienced by a patient. Other analgesics which can be co-administered with the present compounds (either at the same time or at different times) include aspirin, ibuprophen, acetaminophen, opiates, acetaminophen combined with codeine, indomethacin, tricyclic antidepressants, anticonvulsants, serotonin reuptake inhibitors, mixed serotonin-norepinephrine reuptake inhibitors, serotonin receptor agonists and antagonists, cholinergic analgesics, adrenergic agents, and neurokinin antagonists. Other analgesics may be found, for example, in the Merck Manual, 16th Ed. (1992) p. 1409.

The present invention thus includes the use of the present compounds in a pharmaceutical composition to treat pain. In addition, the invention includes the use of these compounds for the manufacture of a medicament for the treatment of pain.

Emesis

The compounds and pharmaceutical compositions of the present application are also useful in alleviating both motion- and toxin-induced emesis, by administering an effective amount of these compounds and/or compositions to a patient in need thereof. Motion sickness as well as emesis associated with the administration of chemotherapeutic agents such as cisplatin, dacarbazine, cyclophosphamide, 5-fluorouracil, doxorubicin and paclitaxol or toxic agents such as soman or sarin can be treated. It is believed that the present compounds can be useful both for motion sickness and for chemical-induced nausea because they have 5-HT1A receptor agonist activity. There are currently no known stategics or agents that are effective in blocking emesis caused from a variety of different stimuli. For example, agents that are known to be effective in blocking motion sickness have not been found to be effective against emesis that is induced chemically.

The present invention thus includes the use of the present compounds in a pharmaceutical composition to treat emesis. In addition, the invention includes the use of these compounds for the manufacture of a medicament for the treatment of emesis.

Neuroregeneration

An additional use of the present compounds and/or pharmaceutical compositions is in stimulating neurogenesis, neuronal regeneration or axo-dendritic complexity in the central and peripheral nervous systems. This is accomplished through the step of administering an effective amount of a compound according to the present invention to a subject in need thereof. Such neuroregenerative effects are believed to be the result of the 5-HT1A receptor agonist activity of the compounds. Neurodegenerative conditions that can be treated can be genetic, spontaneous or iatrogenic, including, but not limited to, stroke, spinal cord injury amyotrophic lateral sclerosis, perinatal hypoxia, ocular damage and retinopathy, ocular nerve degeneration, hearing loss, restless leg syndrome, Gulf War Syndrome and Tourette's syndrome. An example of a drug therapy that is currently used to treat the neurodegenerative disease ALS is the 5-HT1A agonist xaliproden.

The compounds of the present invention can also be used to treat peripheral neuropathies. Examples of diseases associated with peripheral neuropathies include, but are not limed to, acromegaly, hypothyroidism, AIDS, leprosy, Lyme disease, systemic lupus erythematosus, rheumatoid arthritis, Sjogren's Syndrome, periarteritis nodosa, Wegener's granulomatosis, cranial arteritis, sarcoidosis, diabetes, vitamin B12 deficiency, cancer, Gulf War Syndrome and alcoholism. Examples of drug therapies associated with peripheral neuropathies include, but are not limed to oncolytic drugs such as a vinca alkaloid, platinum derivatives such as cisplatin, paclitaxel, suramin, altretamine, carboplatin, chlorambucil, cytarabine, dacarbazine, docetaxel, etoposide, fludarabine, ifosfamide with mesna, tamoxifen, teniposide, or thioguanine.

The present invention thus includes the use of the present compounds in a pharmaceutical composition to treat neurodegeneration or injury. In addition, the invention includes the use of these compounds for the manufacture of a medicament for the treatment of neurodegeneration or injury.

Neuroprotection and Use as Biodefense Agent

An additional aspect of the present invention is a method of stimulating neuronal function involving a mechanism associated with neuroprotection/neuroregeneration in the central or peripheral nervous system of a subject, comprising the step of administering an effective amount of the present compounds and pharmaceutical compositions to the subject. Compounds in this series can be useful in providing neuroprotection against exposure to chemical organo-phosphorus nerve agents. These compounds are believed to target multiple brain substrates expected to have synergistic action in the treatment of multiple toxicities as a result of chemical exposure in biodefense.

Acute high dose exposure to chemical agents results in seizures and/or death. Lower level exposure can result in what has been termed Gulf War Syndrome, which includes neuronal cell loss, acute and/or delayed cognitive impairment, acute and/or delayed attention impairment, and peripheral neuropathy. Other potential indications from exposure to chemical agents include emesis and anxiety.

The present invention thus includes the use of the present compounds in a pharmaceutical composition to provide neuroprotection. In addition, the invention includes the use of these compounds for the manufacture of a medicament for providing neuroprotection.

Dosing

Depending upon the particular needs of the individual subject involved, the compounds of the present invention can be administered in various doses to provide effective treatment concentrations based upon the teachings of the present invention. Factors such as the activity of the selected compounds, the physiological characteristics of the subject, the extent or nature of the subjects disease or condition, and the method of administration will determine what constitutes an effective amount of the selected compounds. Generally, initial doses will be modified to determine the optimum dosage for treatment of the particular subject. The compounds can be administered using a number of different routes including oral administration, topical administration, transdermal administration, intraperitoneal injection, or intravenous injection directly into the bloodstream. Effective amounts of the compounds can also be administered through injection into the cerebrospinal fluid or infusion direly into the brain, if desired.

An effective amount of any embodiment of the present invention is determined using methods known to pharmacologists and clinicians having ordinary skill in the art. For example, a pain relieving effective amount can be determined subjectively by administering increasing amounts of the pharmaceutical compositions of the present invention until such time the patient being treated reports diminishment in pain sensations. Blood levels of the drug can be determined using routine biological and chemical assays and these blood levels can be matched to the route of administration. The blood level and route of administration giving the most desirable level of pain relief can then be used to establish an "effective amount" of the pharmaceutical composition for treating the pain under study. This same method of titrating a pharmaceutical composition in parallel with administration route can be used to ascertain an "effective amount" of the pharmaceutical compositions of the present invention for treating any and all psychiatric or neurological disorders described herein. In addition, animal models as described below can be used to determine applicable dosages for a particular condition.

Exemplary dosages in accordance with the teachings of the present invention for these compounds range from 0.0001 mg/kg to 60 mg/kg, though alternative dosages are contemplated as being within the scope of the present invention. Suitable dosages can be chosen by the treating physician by taking into account such factors as the size, weight, age, and sex of the patient, the physiological state of the patient, the severity of the condition for which the compound is being administered, the response to treatment, the type and quantity of other medications being given to the patient that might interact with the compound, either potentiating it or inhibiting it, and other pharmacokinetic considerations such as liver and kidney function.

Animal Models

In determining the therapeutic effects and appropriate dosages of particular compounds and pharmaceutical compositions according to the present application for a human subject, animal models can be used. Exemplary animal models are set forth below.

The following representative set of compounds of the present application was tested in various animal models:

1-{4-[4-(4-Fluorophenyl)piperazin-1-yl]butyl}-1,5,6,7-tetrahydroindol-4-one

1-{4-[4-(3,4-Dichlorophenyl)piperazin-1-yl]butyl}-1,5,6,7-tetrahydroindol-4-one

1-{2-[4-(3,4-Difluorophenyl)piperazin-1-yl]ethyl}-1,5,6,7-tetrahydroindol-4-one

1-{4-[4-(3,4-Dimethylphenyl)piperazin-1-yl]butyl}-1,5,6,7-tetrahydroindol-4-one

Tail Flick Test (Pain Model)

Tail-flick has been used to define or monitor analgesic levels following exposure to a variety of compounds (D'Amour and Smith, 1941; Harris and Pierson, 1964). It can be used to test mice, rats or monkeys by focusing a beam of light on the tail and evaluating latency to tail-flick. This test has proven useful for screening weak or strong analgesics (Dewey et. al., 1969). The representative compounds listed above were effective in relieving the hard pain induced by a focused beam of light on the tail. An analgesic effect was determined for three of the four compounds tested.

Mouse Writhing Test (Pain Model)

An accepted standard for detecting and comparing the analgesic activity of different classes of analgesic compounds for which there is a good correlation with human analgesic activity is the prevention of acetic acid induced writhing in mice. R. Koster et al., Acetic acid for analgesic screening. Fed. Proc. 18:412 (1959).

Mice, treated with various doses of the present compounds and in combination with another analgesic or with vehicle are injected intraperitoneally with a standard challenge dose of acetic acid 5 minutes prior to a designated observation period. The acetic acid is prepared as a 0.55% solution and injected at a volume of 0.1 ml/10 grams of body weight. For scoring purposes a "writhe" is indicated by whole body stretching or contracting of the abdomen during an observation period beginning about five minutes after the administration of acetic acid. The representitive compounds listed above were effective in relieving the soft pain induced by acetic acid.

Hot Plate Test (Pain Model)

Hot plate is used as a test for drug-induced analgesia to thermal pain. In the performance of this test, a mouse or rat is placed on a heated plate. The latency for the animal to demonstrate a pain response to the heated plate is measured. Pain responses can include hindpaw withdrawal from the plate associated with hindpaw licking or other nocifensive behaviors. A drug-induced delayed latency is indicative of an analgesic response. The representitive compounds listed above were effective in increasing the latency to pain response in the hot plate test.

Plantar Formalin Test (Pain Model)

A subcutaneous injection of a formalin solution into the ventral, or plantar, surface of a rat or mouse hindpaw can induce an acute pain response in the treated paw. The response can include hindpaw withdrawal from the floor associated with hindpaw licking. The time the animal maintains the hindpaw withdrawal from the floor and the number of times the animal turns to lick the hindpaw are measures of pain. An analgesic compound reduces the withdrawal time and number of paw licks. Compounds from this series were effective in reducing the behaviors induced by plantar formalin injection.

Other clinically acceptable pain models can also be used to determine the effects or dosing of a particular compound for use in treating pain, including the following: Chung/Bennett Model; Hargreaves Test; Mechanical Allodynia (von Frey); Paw Plethysmograph Test; Intraperitoneal Irritant Injection-Induced Writhing Test.

Induction and Measurement of Chemotherapy-Induced Emesis (Emesis Model)

Male or female *S. murinus* (30-80 g) are maintained in a temperature-controlled room at 24±1° C. under artificial lighting, with lights on between 0700 and 1730 hours. Artificial humidity is maintained at 50±5%. Animals are allowed free access to water and pelleted cat chow (e.g., Feline Diet 5003, PMI® Feeds, St Louis, USA).

On the day of experiment, the animals are transferred to clear observation chambers (approximately 21×14×13 cm) for the assessment of emetic behavior. They are allowed 30 minutes to adapt before being injected subcutaneously with compounds or their respective vehicles. Chemotherapy emetic agents are administered intravenously following administration of test compounds. The animals are then observed for 60 minutes. An episode of emesis is characterized by rhythmic abdominal contractions that are either associated with the oral expulsion of solid or liquid material from the gastrointestinal tract (i.e. vomiting) or not associated with the passage of material (i.e. retching movements). An episode of retching and/or vomiting is considered separate when an animal changed its location in the observation chamber, or when the interval between retches and/or vomits exceeded 2 seconds. Compounds in this series are effective in blocking chemotherapy-induced emesis.

Induction and Measurement of Motion-Induced Emesis (Emesis Model)

To test for emesis due to motion exposure, animals are placed in a transparent cage on a reciprocal shaker (e.g., Taitec, Double Shaker R-30, Taiyo Scientific Industrial Co Ltd.) after an acclimatization period of at least 5 minutes. Compounds are administered at predetermined time points before testing. The animals are exposed to horizontal motion of 4 cm displacement (2 cm left, 2 cm right) at a frequency of 1 Hz for 10 minutes. A 10 minute exposure is used to reduce the chances of obtaining a false negative result. Observation is continued for at least 5 minutes after the end of motion exposure in case a delayed response occurs, although previous studies have shown that episodes of emesis after cessation of motion are very rare. Compounds in this series are effective in blocking motion-induced emesis.

Pre-Pulse Inhibition Testing (Schizophrenia/Psychosis Model)

The non-competitive NMDA receptor antagonist phencyclidine (PCP) reduces pre-pulse inhibition (PPI) of the acoustic startle response in rodents. Compounds that improve the PCP-induced deficits in pre-pulse inhibition can be useful for treating schizophrenia. In this test, male C-57 mice are assigned to five dose groups of eight animals per group, and vehicle or test compound are administered orally (PO) or subcutaneously (SC) 20 minutes prior to intraperitoneal (EP) administration of vehicle or PCP (5 mg/kg). Ten minutes following PCP administration, the mice are placed into Hamilton-Kinder startle chambers and evaluated. Following a five-minute acclimatization period with background white noise (65 db), mice are exposed to five different trial types. Trials were presented ten-time search in a quasi-random order, with randomized 5 to 25 second inter-trial intervals. The trials are: stimulus only trial (120 db white noise, 50 ms stimulus); two different prepulse+pulse trials in which a 20 ms 5 db, or 10 db stimuli above a 65 db background preceded the 120 db pulse by 120 ms; a 10 db prepulse without a 120 db pulse; and a no stimulus trial, in which only the background noise was presented. Reversal of disruption of pre-pulse inhibition produced by PCP is a clinical predictor of compounds with antipsychotic activity.

Conditioned Avoidance Testing (Schizophrenia/Psychosis Model)

The Condition Avoidance Responding (CAR, active avoidance) model tests for antipsychotic activity. The disruption of avoidance (increased latency) without disruption of escape (extrapyramidal motor function) is a clinical predictor of compounds with antipsychotic activity. Training of animals (mice) consists of 20 trials with variable inter-trial intervals (trained to 80% Avoidance Criteria). After a one-minute acclimation period, the house light and an acoustic 90 dB tone (conditioned stimuli) are presented. A response (crossing to dark compartment) within 5 seconds ends the trial and trial is recorded as avoidance response (CAR). If the mouse does not respond within 5 seconds, foot shock (0.8 mA) is presented, and the response (moving to the dark chamber) during the shock was recorded as an escape response. To avoid shock, animals learn to move from the lighted side of the -chamber to the dark side when the cue is presented (avoidance) or moved when the shock is administered (escape). Vehicle or test compounds are administered subcutaneously 20 minutes before the test session. This checks for disruption of cognition and attention.

Other clinically acceptable models of schizophrenia and/or other psychiatric conditions can also be used to determine the effects or dosing of a particular compound for use in treating psychosis, including the following: Amphetamine-, Cocaine-, PCP-, or MK-801-Induced Hyperlocomotion; Catalepsy, and MK-801-Induced Locomotion and Falling.

Potentiated Startle (Anxiety Model)

Hamilton-Kinder startle chambers were used for conditioning sessions and for the production and recording of startle responses. A classical conditioning procedure was used to produce potentiation of startle responses. Briefly, on the first 2 days, rats were placed into dark startle chambers in which shock grids were installed. Following a 5-minute acclimation period, each rat received a 1 mA electric shock (500 ms) preceded by a 5 second presentation of light (15 watt) which remained on for the duration of the shock. Ten presentations of the light and shock were given in each conditioning session, rats were gavaged with a solution of test compound of water and startle testing sessions were conducted. A block of 10 consecutive presentations of acoustic startle stimuli (110 dB, non-light-paired) were presented at the beginning of the session in order to minimize the influences of the initial rapid phase of habituation to the stimulus. This was followed by 20 alternating trials of the noise alone or noise preceded by the light. Excluding the initial trial block, startle response amplitudes for each trial type (noise–alone vs. light+noise) were averaged for each rat across the entire test session. Data are presented as the difference between noise–alone and light+noise. Compounds that reduce or block potentiated startle are considered to have anxiolytic activity.

Automated Elevated Plus Maze (Anxiety Model)

The Hamilton-Kinder elevated plus-maze is based on the design of Helton et al., and was originally validated for mice by Lister (1987). The maze can be made of Plexiglas having two open arms (e.g., 30×5×0.25 cm) and two enclosed arms (30×5×15 cm). The floor of each maze arm is corrugated to provide texture. The arms extend from a central platform and angled at 90 degrees from each other. The maze iss elevated to a height of 45 cm above the floor and illuminated by red light. Individual infrared photocells are mounted along each arm of the maze to monitor closed, open, or nosepoke activity. Mice are individually placed on the central platform of the maze and the number of closed arm, open arm, and nosepoke (poking head only into open arm from closed arm of maze) counts are recorded and used as a measure of arm entries and time spent on various sections of the maze over a five-minute test period. Administration of the present compounds can increase open arm activity indicating anxiolytic activity.

Other clinically acceptable models of anxiety can also be used to determine the effects or dosing of a particular compound for use in treating anxiety, including the Light/Dark Exploration and Maternal Separation Vocalization Tests.

Tail Suspension Test (Depression Model)

The tail suspension test is a variant of the "behavioral despair" forced swimming test in which immobility is induced by suspending an animal by the tail (Steru et al., 1985). The chamber was 17 cm W×25 cm H×15 cm D with a hook (4 cm) attached to the center of the ceiling. There was no front wall to allow for the observation of the mouse behavior. The mouse was hung on a hook by an adhesive tape placed 15 mm from the extremity of its tail. The animal was positioned with its stomach towards the investigator to assure the observation of the total immobility. Immobility was scored as a sum of the time periods during which the animal hung passively and motionless for at least 2 sec. The total period of observation was 6 min. Administration of the representitive compounds listed above was effective in reducing immobility in the test.

Other clinically acceptable models of depression can also be used to determine the effects or dosing of a particular compound for use in treating depression, including the Forced Swim Test and DRL Test.

Measures of CNS Activity

Acoustic startle is a test for sensorimotor reactivity and can be used to profile the potential for drug-induced adverse side-effects. Acoustic startle is measured as the maximum force (N) transduced to a plate in response to a 120 dB stimulus. Hamilton-Kinder startle chambers were used to present the startle stimulus and measure and record the response. Animals were presented a block of 20 consecutive acoustic stimuli and the responses were averaged. A drug-induced increase in response can indicate the potential for an adverse event such as anxiogenic potential for that dose. A drug-induced decrease in response can indicate, the potential for an adverse event such as sedation for that dose. The representitive compounds listed above do not induce a significant increase or decrease in acoustic startle response at efficacy doses tested. At higher than efficacy doses, compounds from this series induce a dose dependent decrease in acoustic startle.

Ambulatory and non-ambulatory activity is used to test spontaneous and drug-induced motor activity. The test can be used to profile the potential for a drug to induce hyperactivity or sedation. A Hamilton-Kinder photobeam activity monitors were used to record the ambulatory and non-ambulatory motor activity of mice and rats. The monitors track the photobeam breaks made by the animal that are used to calculate the number of ambulatory and fine (non-ambulatory) motor movements. A drug-induced increase in activity can indicate the potential for an adverse event such as hyperactivity. A drug-induced decrease in response can indicate the potential for an adverse event such as sedation. Compounds from this series do not induce a significant increase or decrease in activity at efficacy doses tested. At higher than efficacy doses, compounds from this series induce a dose dependent decrease in activity.

Additional Models

Other clinically accepted models of neurological conditions known to the art can also be used to determine the therapeutic effects and appropriate dosages of particular compounds and pharmaceutical compositions according to the present application. These include, inter alia, the following tests.

Learning Memory Models: Acquisition of Fear Potentiated Startle; Passive Avoidance, Shuttle or Step Down; Acquisition of Active Avoidance; Morris Water Maze; and Amnesic Reversal.

Attention Deficit Models: ADHD Young Animal Model (PPI and Activity); ADD Aged Animal Model; and Acquisition of Active Avoidance Model.

Neuroprotectuon/Epilepsy: Pentylenetetrazol-, Strychnine-, Bicuculine-, Picrotoxin-Induced Convulsions, sarin and soman and MES/ECS.

Parkinson's Disease: Apomorphine-, Amphetamine-Induced Rotations (6-OHDA); and Reserpine-Induced Hypothermia/Hypolocomotion.

Drug Dependence and Withdrawal: Nicotine-, Benzodiazepine-, and Ethanol-Induced Withdrawal.

Pharmaceutical Compositions

Another aspect of the present invention is a pharmaceutical composition that comprises: (1) an effective amount of a compound according to the present invention as described above (including salts and esters thereof); and (2) a pharmaceutically acceptable excipient.

A pharmaceutically acceptable excipient, including carriers, can be chosen from those generally known in the art including, but not limited to, inert solid diluents, aqueous solutions, or non-toxic organic solvents, depending on the route of administration. If desired, these pharmaceutical formulations can also contain preservatives and stabilizing agents and the like, for example substances such as, but not limited to, pharmaceutically acceptable excipients selected from the group consisting of wetting or emulsifying agents, pH buffering agents, human serum albumin, antioxidants, preservatives, bacteriostatic agents, dextrose, sucrose, trehalose, maltose, lecithin, glycine, sorbic acid, propylene glycol, polyethylene glycol, protamine sulfate, sodium chloride, or potassium chloride, mineral oil, vegetable oils and combinations thereof. Those skilled in the art will appreciate that other carriers also can be used.

Liquid compositions can also contain liquid phase excipients either in addition to or to the exclusion of water. Examples of such additional liquid phases are glycerin, vegetable oils such as cottonseed oil, organic esters such as ethyl oleate, and water-oil emulsions.

Formulations suitable for parenteral administration, such as, for example, by intravenous, intramuscular, intradermal, and subcutaneous routes, include aqueous and non-aqueous isotonic sterile injection solutions. These can contain antioxidants, buffers, preservatives, bacteriostatic agents, and solutes that render the formulation isotonic with the blood of the particular recipient. Alternatively, these formulations can be aqueous or non-aqueous sterile suspensions that can include suspending agents, thickening agents, solubilizers, stabilizers, and preservatives. The pharmaceutical compositions of the present invention can be formulated for administration by intravenous infusion, oral, topical, intraperitoneal, intravesical, transdermal, intranasal, rectal, vaginal, intramuscular, intradermal, subcutaneous and intrathecal routes.

Formulations of compound suitable for use in methods according to the present invention can be presented in unit-dose or multi-dose sealed containers, in physical forms such as ampules or vials. The compositions can be made into aerosol formations (i.e., they can be "nebulized") to be administered via inhalation. Aerosol formulations can be placed into pressurized acceptable propellants, such as dichloromethane, propane, or nitrogen. Other suitable propellants are known in the art.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference to their entirety. In addition, all groups described herein can be optionally substituted unless such substitution is excluded.

Groupings of alternative elements or embodiments of the invention disclosed herein are not to be construed as limitations. Each group member can be referred to and claimed individually or in any combination with other members of the group or other elements found herein. It is anticipated that one or more members of a group can be included in, or deleted from, a group.

What is claimed is:

1. A pharmaceutical composition comprising a compound having the following formula (I):

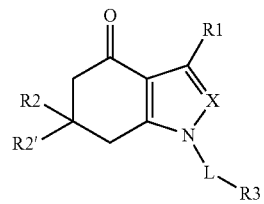

wherein:
(a) X is CH or N;
(b) $R_1$ is hydrogen, alkyl, aralkyl, heteroaralkyl, alkenyl, aralkenyl, heteroaralkenyl, aryl, or heteroaryl;
(c) $R_2$ is hydrogen, alkyl, aralkyl, aryl, or heteroaryl;
(d) $R_{2'}$ is hydrogen unless $R_2$ is methyl, in which case $R_{2'}$ is also methyl;
(e) $R_3$ has the following formula (III):

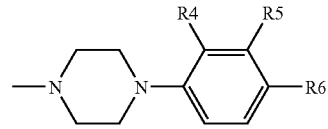

wherein:
(i) $R_4$ is hydrogen, alkyl, halo, hydroxy, alkoxy, cyano, nitro, perfluoroalkyl, perfluoroalkoxy, or hydroxymethyl;
(ii) $R_5$ is hydrogen, alkyl, halo, alkoxy, cyano, nitro, perfluoroalkyl, perfluoroalkoxy, amino, aminocarbonyl, aminosulfonyl, or hydroxymethyl;
(iii) $R_6$ is alkyl, halo, alkoxy, perfluoroalkyl, perfluoroalkoxy, or nitro;
(iv) $R_4$ and $R_5$ when taken together can form a 5 or 6 membered ring and can contain one or more heteroatoms;

(v) wherein $R_5$ and $R_6$ when taken together are selected from the group consisting of a methylenedioxy group and an ethylenedioxy group;

(f) L is an alkyl substituted hydrocarbyl moiety of the formula (IV):

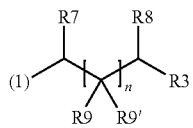

wherein:
(i) n is 0, 1 or 2;
(ii) R7 and R8 is ethyl;
(iii) R9 and R9' is ethyl;
if n is 1 and R7 or R8 is methyl or ethyl, then R9 and R9' are hydrogen;
if n is 1 and R7 and R8 are hydrogen, then R9 and R9' are methyl or ethyl; and
if n is 2, then R9 and R9' are hydrogen and one or both of R7 and R8 are methyl or ethyl,
and pharmaceutically acceptable salts and esters thereof.

2. A pharmaceutical composition comprising a compound having the following formula (I):

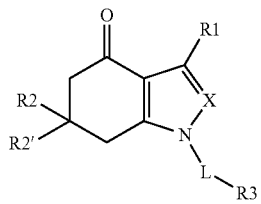

wherein:
(a) X is CH or N;
(b) $R_1$ is hydrogen, alkyl, aralkyl, heteroaralkyl, alkenyl, aralkenyl, heteroaralkenyl, aryl, or heteroaryl;
(c) $R_2$ is hydrogen, alkyl, aralkyl, aryl, or heteroaryl;
(d) $R_{2'}$ is hydrogen unless $R_2$ is methyl, in which case $R_{2'}$ is also methyl;
(e) $R_3$ has the following formula (III):

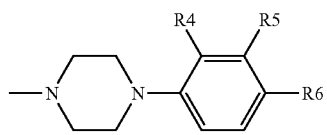

wherein:
(i) $R_4$ is hydrogen, alkyl, halo, hydroxy, alkoxy, cyano, nitro, perfluoroalkyl, perfluoroalkoxy, or hydroxymethyl;
(ii) $R_5$ is hydrogen, alkyl, halo, alkoxy, cyano, nitro, perfluoroalkyl, perfluoroalkoxy, amino, aminocarbonyl, aminosulfonyl, or hydroxymethyl;
(iii) $R_6$ is alkyl, halo, alkoxy, perfluoroalkyl, perfluoroalkoxy, or nitro;
(iv) $R_4$ and $R_5$ when taken together can form a 5 or 6 membered ring and can contain one or more heteroatoms;

(v) R5 and R6 when taken together can form a 5 or 6 membered ring and can contain one or more heteroatoms;

(f) wherein L is an alkyl substituted hydrocarbyl moiety of formula (IV):

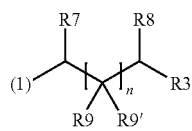

wherein:
(i) n is 1 or 2;
(ii) R7 and R8 is ethyl;
(iii) R9 and R9' is ethyl;
if n is 1 and R7 or R8 is methyl or ethyl, then R9 and R9' are hydrogen;
if n is 1 and R7 and R8 are hydrogen, then R9 and R9' are methyl or ethyl; and
if n is 2, then R9 and R9' are hydrogen and one or both of R7 and R8 are methyl or ethyl,
and pharmaceutically acceptable salts and esters thereof.

3. A pharmaceutical composition comprising a compound selected from the group consisting of:
1-{4-[4-(4-Fluorophenyl)piperazin-1-yl]butyl}-1,5,6,7-tetrahydroindol-4-one;
1-{3-[4-(3,4-Dichlorophenyl)piperazin-1-yl]propyl}-1,5,6,7-tetrahydroindol-4-one;
1-{4-[4-(2,4-Dichlorophenyl)piperazin-1-yl]butyl}-1,5,6,7-tetrahydroindol-4-one;
1-{4-[4-(3-Chloro-4-fluorophenyl)piperazin-1-yl]butyl}-1,5,6,7-tetrahydroindol-4-one;
1-{4-[4-(4-Bromophenyl)piperazine-1-yl]butyl}-1,5,6,7-tetrahydroindol-4-one; and
1-{4-[4-(3,4-dichlorophenyl)piperazin-1-yl]butyl}-1,5,6,7-tetrahydroindol-4-one,
and pharmaceutically acceptable salts and esters thereof.

4. The pharmaceutical composition of claim 3, wherein the compound is 1-{4-[4-(3,4-dichlorophenyl)piperazin-1-yl]butyl}-1,5,6,7-tetrahydroindol-4-one.

5. A pharmaceutical composition comprising a compound having the following formula (I):

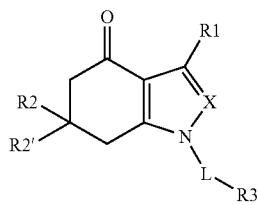

wherein:
(a) X is CH or N;
(b) $R_1$ is hydrogen, alkyl, aralkyl, heteroaralkyl, alkenyl, aralkenyl, heteroaralkenyl, aryl, or heteroaryl;
(c) $R_2$ is hydrogen, alkyl, aralkyl, aryl, or heteroaryl;
(d) $R_{2'}$ is hydrogen unless $R_2$ is methyl, in which case $R_{2'}$ is also methyl;
(e) $R_3$ has the following formula (III):

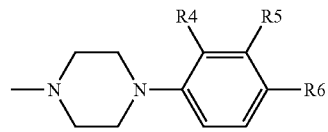

wherein:
(i) $R_4$ is hydrogen, alkyl, halo, hydroxy, alkoxy, cyano, nitro, perfluoroalkyl, perfluoroalkoxy, or hydroxymethyl;
(ii) $R_5$ is hydrogen, alkyl, halo, alkoxy, cyano, nitro, perfluoroalkyl, perfluoroalkoxy, amino, aminocarbonyl, aminosulfonyl, or hydroxymethyl;
(iii) $R_6$ is halo;
(iv) $R_4$ and $R_5$ when taken together can form a 5 or 6 membered ring and can contain one or more heteroatoms;
(v) $R_5$ and $R_6$ when taken together can form a 5 or 6 membered ring and can contain one or more heteroatoms;
(f) L is an alkyl substituted hydrocarbyl moiety of the formula (IV):

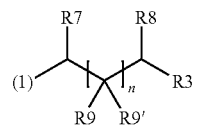

wherein:
(i) n is 1 or 2;
(ii) R7 and R8 is ethyl;
(iii) R9 and R9' is ethyl;
if n is 1 and R7 or R8 is methyl or ethyl, then R9 and R9' are hydrogen;
if n is 1 and R7 and R8 are hydrogen, then R9 and R9' are methyl or ethyl; and
if n is 2, then R9 and R9' are hydrogen and one or both of R7 and R8 are methyl or ethyl,
and pharmaceutically acceptable salts and esters thereof.

6. The pharmaceutical composition of claim 5, wherein $R_5$ and $R_6$ are halo.

* * * * *